(12) United States Patent
Lee et al.

(10) Patent No.: US 11,730,547 B2
(45) Date of Patent: *Aug. 22, 2023

(54) TRACKING SYSTEM AND TRACKING METHOD USING SAME

(71) Applicants: KOH YOUNG TECHNOLOGY INC., Seoul (KR); KYUNGPOOK NATIONAL UNIVERSITY INDUSTRY-ACADEMIC COOPERATION FOUNDATION, Daegu (KR)

(72) Inventors: Hyun Ki Lee, Daegu (KR); Hyun Min Oh, Daegu (KR); Min Young Kim, Daegu (KR)

(73) Assignees: KOH YOUNG TECHNOLOGY INC., Seoul (KR); KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 293 days.

This patent is subject to a terminal disclaimer.

(21) Appl. No.: 17/024,037

(22) Filed: Sep. 17, 2020

(65) Prior Publication Data
US 2021/0000551 A1   Jan. 7, 2021

Related U.S. Application Data

(63) Continuation of application No. 15/503,565, filed as application No. PCT/KR2015/008412 on Aug. 11, 2015, now Pat. No. 10,799,299.

(30) Foreign Application Priority Data

Aug. 13, 2014 (KR) .................... 10-2014-0104889

(51) Int. Cl.
*A61B 34/20* (2016.01)
*A61B 90/00* (2016.01)

(52) U.S. Cl.
CPC .............. *A61B 34/20* (2016.02); *A61B 90/39* (2016.02); *A61B 2034/2048* (2016.02);
(Continued)

(58) Field of Classification Search
CPC .... A61B 2034/2048; A61B 2034/2055; A61B 2034/2057; A61B 2090/0818; A61B 2090/3983; A61B 34/20; A61B 90/39
See application file for complete search history.

(56) References Cited

U.S. PATENT DOCUMENTS 5,592,401 A    1/1997  Kramer
10,799,299 B2 * 10/2020  Lee .................. A61B 34/20
(Continued)

FOREIGN PATENT DOCUMENTS

CN    102470014    5/2012
CN    103189013    7/2013
(Continued)

OTHER PUBLICATIONS

International Search Report for International Application No. PCT/KR2015/008412 with English translations, dated Sep. 14, 2015.
(Continued)

*Primary Examiner* — Michael T Rozanski
(74) *Attorney, Agent, or Firm* — Kile Park Reed & Houtteman PLLC

(57) ABSTRACT

A tracking system and a tracking method using the same are disclosed. The tracking system includes a marker, a camera unit, a first inertial measuring unit, a second inertial measuring unit and a tracking processing unit. The marker is fixed on the measurement object, and the camera unit outputs a marker image by photographing the marker. The
(Continued)

first inertial measuring unit is fixed on the camera unit, and measures and outputs first inertia comprising first accelerated velocity and first angular velocity. The second inertial measuring unit is fixed to one of the measurement object and the marker, and measures and outputs second inertia comprising second accelerated velocity and second angular velocity. The tracking processing unit primarily extracts the position and the posture of the measurement object using the marker image, and secondarily extracts the position and the posture of the measurement object using the first and second inertias.

5 Claims, 6 Drawing Sheets

(52) U.S. Cl.
CPC .......... *A61B 2034/2055* (2016.02); *A61B 2034/2057* (2016.02); *A61B 2090/0818* (2016.02); *A61B 2090/3983* (2016.02)

(56) References Cited

U.S. PATENT DOCUMENTS

| | | |
|---|---|---|
| 2009/0247863 A1 | 10/2009 | Proulx et al. |
| 2009/0248044 A1 | 10/2009 | Amiot et al. |
| 2010/0194879 A1 | 8/2010 | Pasveer et al. |
| 2012/0108954 A1 | 5/2012 | Schulhauser et al. |
| 2014/0088410 A1 | 3/2014 | Wu |
| 2014/0107471 A1 | 4/2014 | Haider et al. |

FOREIGN PATENT DOCUMENTS

| | | |
|---|---|---|
| DE | 10 2011 054 730 | 4/2013 |
| EP | 2 570 890 | 3/2013 |
| JP | 2010-534316 | 11/2010 |
| JP | 2011-517971 | 6/2011 |
| KR | 10-2013-0137435 | 12/2013 |
| WO | 00/39576 | 7/2000 |
| WO | 2009/007917 | 1/2009 |
| WO | 2011/001301 | 1/2011 |
| WO | 2012/152264 | 11/2012 |
| WO | 2013/053397 | 4/2013 |
| WO | 2014/052428 | 4/2014 |

OTHER PUBLICATIONS

Chinese Office Action with English Translation for Chinese Application No. 201580043386.7, dated Aug. 27, 2018.
Chinese Office Action with English translation corresponding to Chinese Application or Publication No. 201580043386.7, dated Jun. 3, 2019.
Indian Office Action, with English translation, corresponding to Indian Application No. 201717008434, dated Feb. 18, 2020.
Chinese Office Action, with English translation, corresponding to Chinese Application or Patent No. 201580043386.7, dated Dec. 30, 2019.

\* cited by examiner

TRACKING SYSTEM AND TRACKING METHOD USING SAME

CROSS REFERENCE TO RELATED APPLICATIONS

This application is a continuation application of U.S. patent application Ser. No. 15/503,565, filed Feb. 13, 2017, the disclosure of which is herein incorporated by reference in its entirety. The U.S. patent application Ser. No. 15/503,565 is a national entry of International Application No. PCT/KR2015/008412, filed on Aug. 11, 2015, which claims priority to Korean Application No. 10-2014-0104889 filed on Aug. 13, 2014, respectively, the entire contents of which are incorporated herein by reference.

TECHNICAL FIELD

The present disclosure relates to a tracking system and a tracking method using the same and, more specifically, to the tracking system, which can track the position of an instrument such as a surgical instrument, and the tracking method using the same.

BACKGROUND ART

A surgical instrument should be placed at an accurate position in a surgical operation, and thus requires a system, which can accurately track the position and posture of the surgical instrument in real time, that is, a tracking system. The tracking system includes an optical tracker using a stereo camera.

The optical tracker is a device which can track the position and posture of the surgical instrument by photographing a marker fixed to the surgical instrument, using the stereo camera. However, when the marker fixed to the surgical instrument is not photographed by the stereo camera, that is, when a problem of occlusion occurs, the optical tracker cannot track the position and posture of the surgical instrument any longer.

Therefore, several recent studies have attempted to solve the above-described problem, additionally using an Inertial Measurement Unit (IMU) fixed to a surgical instrument or a marker. The IMU is a sensor device which can measure and acquire acceleration and angular velocity of the surgical instrument, and can track the position and posture of the surgical instrument using the acquired acceleration and angular velocity. Therefore, even when the problem of occlusion occurs in a stereo camera, the IMU can overcome the problem and thus enables continuously tracking of the position and posture of the surgical instrument.

However, the acceleration measured by the IMU includes both gravitational acceleration caused by the Earth's gravity and movement acceleration caused by movement. Herein, only the movement acceleration is used for tracking the position of the surgical instrument, and it is necessary to remove the gravitational acceleration from the acceleration measured by the IMU. Therefore, in order to remove the gravitational acceleration from the acceleration measured by the IMU, a correction between the earth's coordinate system corresponding to the gravitational acceleration and an optical tracker coordinate system corresponding to the acceleration measured by the IMU is necessary.

However, when the correction between the earth's coordinate system and the optical tracker coordinate system has been made, the optical tracker should not be moved. If the optical tracker moves, the optical tracker coordinate system changes by the movement of the optical tracker, and thus the re-correction of the coordinate system is required. The coordinate system re-correction process is not only cumbersome, but may also prevent recognition of the necessity for a coordinate system correction when there is an unintentional change in the position of an optical tracker during a surgical operation.

SUMMARY

For the purpose of solving the problems described above, an aspect of the present disclosure provides a tracking system which can continuously track a position and posture of a measurement object, regardless of the movement of an optical tracker.

Further, another aspect of the present disclosure provides a tracking method using the tracking system.

A tracking system according to an embodiment of the present disclosure includes: a marker; a camera unit; a first inertia measurement unit; a second inertia measurement unit; and a tracking processing unit.

The marker is fixed to a measurement object. The camera unit photographs the marker and outputs a marker image. The first inertia measurement unit is fixed to the camera unit, and measures and outputs first inertia including first acceleration and first angular velocity. The second inertia measurement unit is fixed to one of the measurement object and the marker, and measures and outputs second inertia including second acceleration and second angular velocity. The tracking processing unit primarily extracts a position and posture of the measurement object, using the marker image, and secondarily extracts the position and posture of the measurement object, using the first inertia and the second inertia.

The tracking processing unit may extract the position of the measurement object, using the first acceleration and the second acceleration, and may extract the posture of the measurement object, using the first angular velocity and the second angular velocity.

The tracking processing unit may extract movement acceleration by the movement of the measurement object from the second acceleration, using gravitational acceleration extracted from the first acceleration, and then extract the position of the measurement object, using the movement acceleration.

The tracking processing unit may extract the gravitational acceleration from the first acceleration, convert at least one of the second acceleration and the gravitational acceleration so that coordinate systems of the second acceleration and the gravitational acceleration coincide with each other, and then extract the movement acceleration, using the second acceleration and the gravitational acceleration having the coincided coordinate systems.

A tracking method according to an embodiment of the present disclosure includes: photographing, by a camera unit, a marker fixed to an measurement object and outputting a marker image; primarily extracting, by a tracking processing unit, a position and posture of the measurement object from the marker image; measuring and outputting, by a first inertia measurement unit fixed to the camera unit, first inertia including first acceleration and first angular velocity; measuring and outputting, by a second inertia measurement unit fixed to one of the measurement object and the marker, second inertia including second acceleration and second angular velocity; and secondarily extracting, by the tracking processing unit, the position and posture of the measurement object using the first inertia and the second inertia.

Secondarily extracting the position and posture of the measurement object may include: extracting the position of the measurement object, using the first acceleration and the second acceleration; and extracting the posture of the measurement object, using the first angular velocity and the second angular velocity.

Extracting the position of the measurement object may include: extracting movement acceleration by the movement of the measurement object from the second acceleration, using gravitational acceleration extracted from the first acceleration; and extracting the position of the measurement object, using the movement acceleration.

Extracting the movement acceleration may include: extracting the gravitational acceleration from the first acceleration; converting at least one of the second acceleration and the gravitational acceleration so that coordinate systems of the second acceleration and the gravitational acceleration coincide with each other; and extracting movement acceleration, using the second acceleration and the gravitational acceleration having the coincided coordinate systems.

When the first inertia measurement unit has a first inertial coordinate system and the second inertia measurement unit has a second inertial coordinate system, converting the at least one of the second acceleration and the gravitational acceleration so that coordinate systems of the second acceleration and the gravitational acceleration coincide with each other may include: converting the gravitational acceleration according to the first inertial coordinate system into the second inertial coordinate system; and removing the gravitational acceleration, which has been converted into the second inertial coordinate system, from the second acceleration to thereby extract the movement acceleration.

When the marker has a marker coordinate system and the camera unit has a camera coordinate system, converting the gravitational acceleration according to the first inertial coordinate system into the second inertial coordinate system may include: converting the gravitational acceleration according to the first inertial coordinate system into the camera coordinate system; converting the gravitational acceleration, which has been converted into the camera coordinate system, into the marker coordinate system; and converting the gravitational acceleration, which has been converted into the marker coordinate system, into the second inertial coordinate system.

When the camera unit has a camera coordinate system, extracting the position of the measurement object, using the movement acceleration, may include: converting the movement acceleration into the camera coordinate system; and extracting the position of the measurement object, using the movement acceleration converted into the camera coordinate system.

Meanwhile, the first acceleration coincides with the gravitational acceleration, and the first angular velocity may be zero (0).

As described above, according to a tracking system and a tracking method using the same according to the present disclosure, as a first inertia measurement unit is fixed to a camera unit which is in a stopped state, the first inertia measurement unit may measure gravitational acceleration. A second inertia measurement unit may be fixed to the marker or the measurement object and measure the acceleration and angular velocity of the measurement object. Thereafter, the gravitational acceleration may be removed from the acceleration of the measurement object so as to extract movement acceleration of the measurement object, and the position and posture of the measurement object may be continuously tracked, using the movement acceleration and the angular velocity of the measurement object.

Further, as the first inertia measurement unit is fixed to the camera unit, even when the camera unit is moved, a conversion relationship between a coordinate system in the first inertia measurement unit and a coordinate system in the camera unit can be maintained to be constant. As a result, it is possible to omit a coordinate system correction of the gravitational acceleration according to the movement of the camera unit and thereby simplify a tracking process.

DETAILED DESCRIPTION

The present disclosure may have various modifications and embodiments and thus will be described in detail by exemplifying specific embodiments through the drawings.

However, it should be understood that the present disclosure is not limited to the specific embodiments, but the present disclosure includes all modifications, equivalents, and alternatives within the spirit and the scope of the present disclosure. Although the terms "ordinal numbers" such as first, second and the like may be used to describe various structural elements, the structural elements should not be limited by the terms. The terms are used merely for the purpose of distinguishing one element from any other element. For example, a first element may be termed a second element, and similarly, a second element may be termed a first element, without departing from the scope of the present disclosure.

In the present application, terms are merely used to describe specific embodiments, and are not intended to limit the present disclosure. As used herein, singular forms may include plural forms as well unless the context clearly indicates otherwise. In the present specification, it should be understood that the terms "include" and "have" indicate the existence of a feature, a number, a step, an operation, a structural element, parts, or a combination thereof, and do not previously exclude the existence or probability of addition of one or more other features, numbers, steps, operations, structural elements, parts, or combinations thereof.

Hereinafter, preferred embodiments of the present disclosure will be described with reference to the accompanying drawings.

Figure 1:
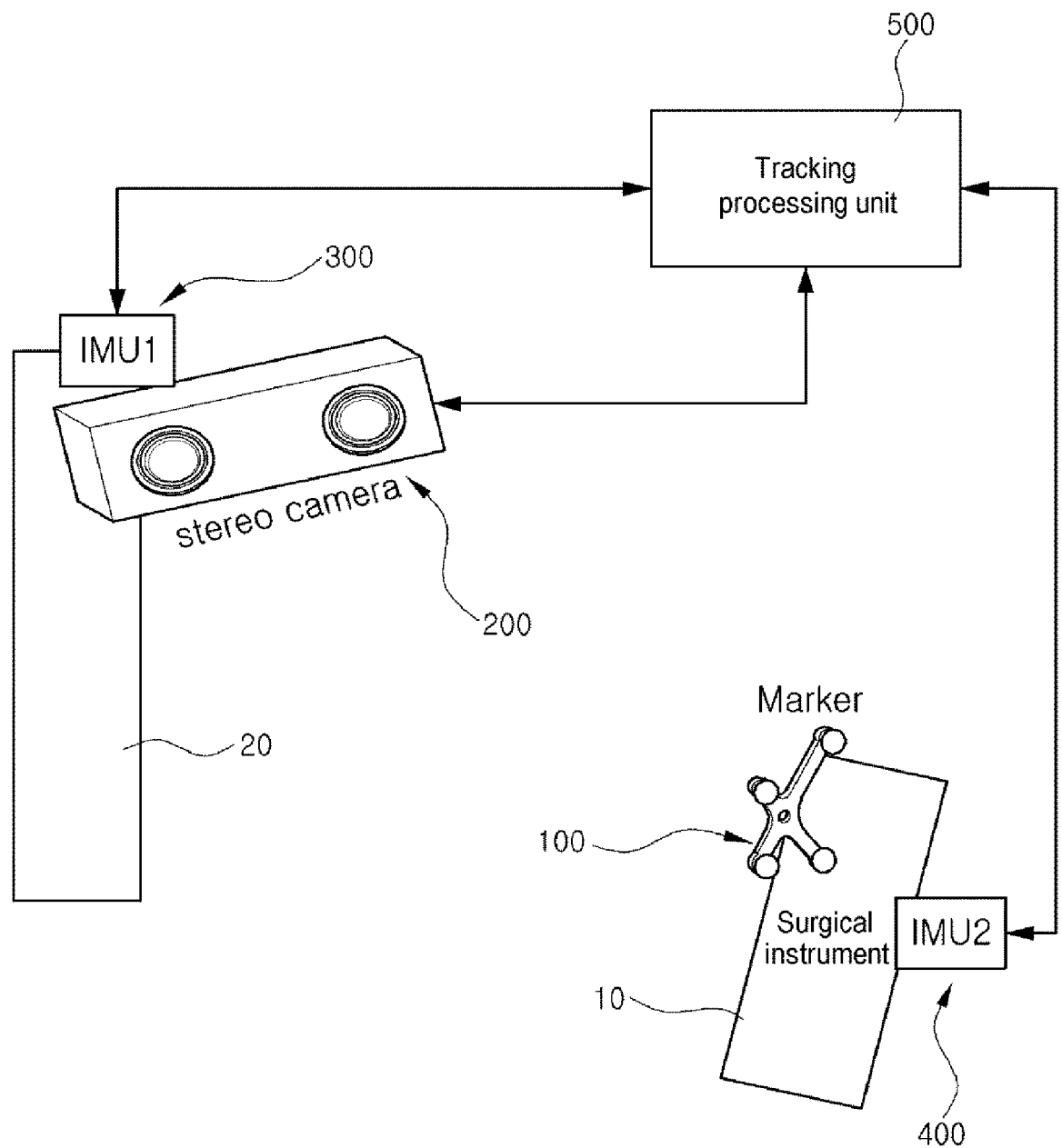
FIG. 1 is a diagram showing a concept of a tracking system according to an embodiment of the present disclosure.

FIG. 1 is a diagram for illustrating a concept of a tracking system according to an embodiment of the present disclosure.

Referring to FIG. 1, the tracking system according to the present disclosure is a device which can track the position and posture of a measurement object 10, and includes: a marker 100; a camera unit 200; a first inertia measurement unit 300; a second inertia measurement unit 400; and a tracking processing unit 500. In this case, the measurement object 10 may be, for example, a surgical instrument.

Meanwhile, in the present embodiment, "the position of the measurement object 10" may refer to a three-dimensional coordinate value of a predetermined point in the measurement object 10, and "the posture of the measurement object 10" may refer to an angle at which the measurement object 10 is spatially or two-dimensionally inclined with respect to an imaginary vertical line. In this case, when the measurement object 10 is not completely spherical, that is, when the measurement object 10 has a shape elongated to any one side, an angle at which the measurement object 10 is inclined with respect to the imaginary vertical line may be formed. Therefore, "the posture of the measurement object 10" may be numerically expressed.

The marker 100 is disposed on and fixed to one side of the measurement object 10. As a result, when a movement occurs in the measurement object 10, the marker 100 may move together with the measurement object 100. The marker 100 may include a plurality of position points in order to measure the position and posture of the measurement object 10. For example, the marker 100 may include four position points as in FIG. 1. Meanwhile, the marker 100 has a maker coordinate system indicative of a three-dimensional position and movement relationship with reference to the marker 100.

The camera unit 200 photographs the marker 100 and outputs a marker image. The camera unit 200 may be disposed on or fixed to a separate holding means 20 so that the camera unit 200 can easily photograph the marker 100. The camera unit 200 may be, for example, a stereo camera which can accurately measure special position and posture information. Meanwhile, the camera unit 200 has a camera coordinate system, which indicates a three-dimensional position and movement relationship with reference to the camera unit 200. Here, a reference coordinate system for indicating the position and posture of the measurement object 10 may be a camera coordinate system.

The first inertia measurement unit 300 is disposed on and fixed to one side of the camera unit 200. The first inertia measurement unit 300 has a first inertial coordinate system, which indicates a three-dimensional position and movement relationship with reference to the first inertia measurement unit 300. Therefore, when the camera unit 200 moves, the first inertia measurement unit 300 moves together with the camera unit 200, and when the camera unit 200 is in a stopped state, the first inertia measurement unit 300 is in a stopped state. Thus, a conversion relationship between the camera coordinate system and the first inertial coordinate system may be always constant.

The first inertia measurement unit 300 includes a sensor which can measure inertia including acceleration and angular velocity. The first inertia measurement unit 300 may be, for example, an Inertial Measurement Unit (IMU). Therefore, the first inertia measurement unit 300 measures and outputs first inertia including first acceleration and first angular velocity. Meanwhile, it is desirable that the camera unit 200 is in a stopped state when measuring the marker 100. If the camera unit 200 is in a stopped state, the first acceleration coincides with gravitational acceleration by the Earth's gravity, and the first angular velocity has a value of zero (0).

The second inertia measurement unit 400 is disposed on and fixed to one of the measurement object 10 and the marker 100. The second inertia measurement unit 400 has a second inertial coordinate system which indicates a three-dimensional position and movement relationship with reference to the second inertia measurement unit 400. Therefore, when the measurement object 10 moves, the marker 100 and the second inertia measurement unit 400 move together with the measurement object 10, and, when the measurement object 10 is in a stopped state, the marker 100 and the second inertia measurement unit 400 are in a stopped state together with the measurement object 10. Thus, a conversion relationship between the marker coordinate system and the second inertial coordinate system may be always constant.

The second inertia measurement unit 400 includes a sensor which can measure inertia including acceleration and angular velocity. The second inertia measurement unit 400 may be, for example, an Inertial Measurement Unit (IMU). Therefore, the second inertia measurement unit 400 measures and outputs second inertia including second acceleration and second angular velocity. In this case, the second inertia refers to a physical quantity according to the movement of the measurement object 10.

The tracking processing unit 500 may transmit or receive signals to or from the camera unit 200, the first inertia measurement unit 300, and the second inertia measurement unit 400 in a wired or wireless communication manner. Therefore, the tracking processing unit 500 may be provided with the marker image from the camera unit 200, the first inertia from the first inertia measurement unit 300, and the second inertia from the second inertia measurement unit 400.

Above all, the tracking processing unit 500 may analyze the marker image and primarily extract the position and posture of the measurement object 10. For example, the tracking processing unit 500 may analyze the positions, sizes, etc. of position points of the marker from the marker image, and calculate the position and posture of the measurement object 10. In this case, the position and posture of the measurement object 10 may be expressed according to the camera coordinate system.

Second, the tracking processing unit 500 may secondarily extract the position and posture of the measurement object 10, using the first inertia and the second inertia. Herein, "secondarily extracting the position and posture of the measurement object 10" may include "only when the primary extraction by analysis of the marker image is impossible, extracting the position and posture of the measurement object 10 in order to complement the same" and "separately extracting the position and posture of the measurement object 10 regardless of the primary extraction by analysis of the marker image". Further, "when the primary extraction by analysis of the marker image is impossible" may include "when the marker has not been photographed because the marker has been occluded by an object" and "when it is impossible to analyze the marker image although the marker image has been acquired".

Meanwhile, when acceleration of an object is doubly integrated, the relative position of the object may be calculated. When the angular velocity of the object is integrated, the relative angle of the object may be calculated. When the initial position and initial tilted angle of the object can be obtained, the position and posture of the object may be calculated. Therefore, the tracking processing unit 500 may secondarily extract the position and posture of the measurement object 10 in the above-described calculation manner. In other words, the tracking processing unit 500 may extract the position of the measurement object 10, using the first acceleration and the second acceleration, and may extract the posture of the measurement object 10, using the first angular velocity and the second angular velocity.

In the process of extracting the position of the measurement object 10, using the first acceleration and the second acceleration, the tracking processing unit 500 may extract movement acceleration by the movement of the measurement object 10 from the second acceleration, using the gravitational acceleration extracted from the first acceleration, and then extract the position of the measurement object 10, using the movement acceleration. Here, in the process of extracting the movement acceleration by the movement of the measurement object 10, the tracking processing unit 500 may extract the gravitational acceleration from the first acceleration, convert at least one of the second acceleration and the gravitational acceleration so that coordinate systems of the second acceleration and the gravitational acceleration coincide with each other, and then extract the movement acceleration, using the second acceleration and the gravitational acceleration having the coincided coordinate systems.

Hereinafter, a tracking method for tracking the position and posture of the measurement object 10, using the above-described tracking system, will be described in detailed.

Figure 2:
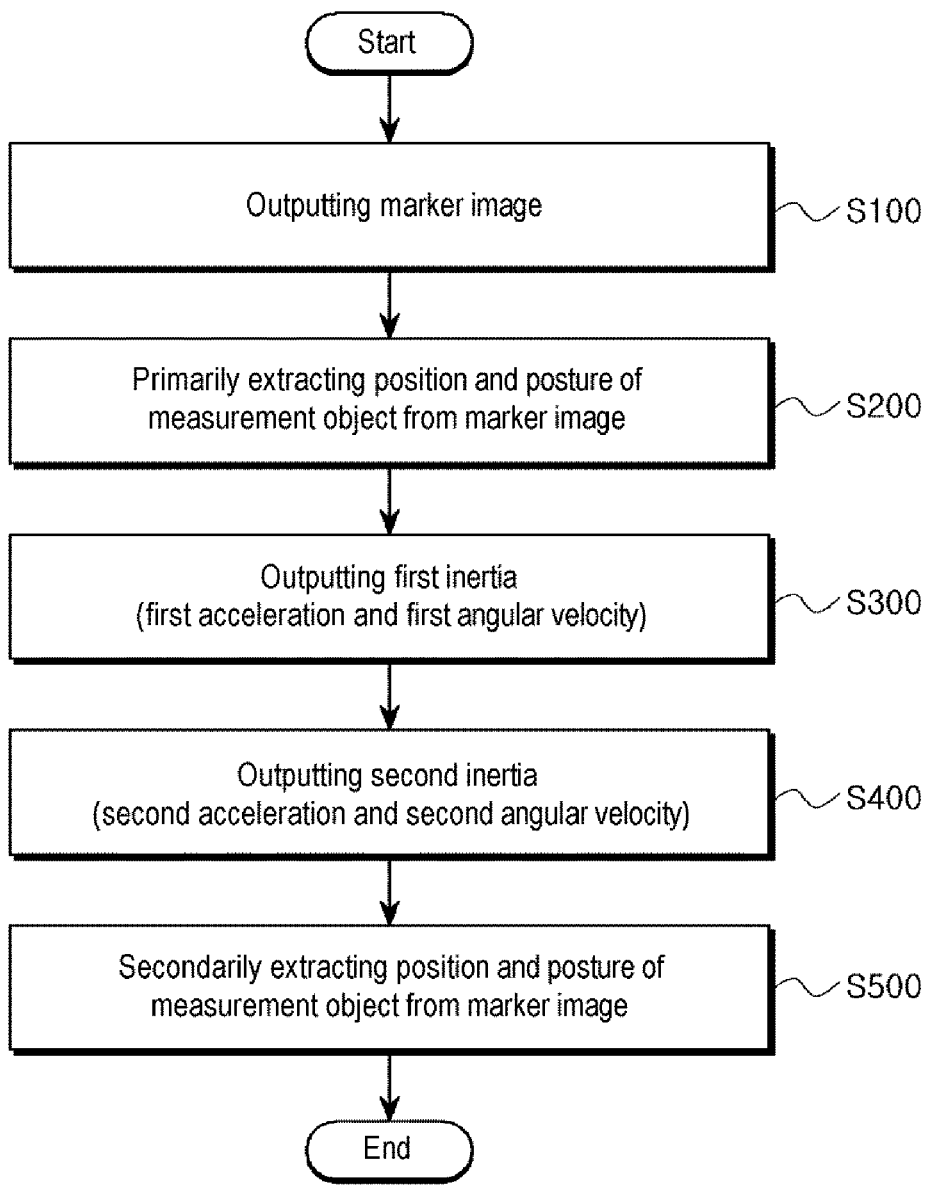
FIG. 2 is a flowchart showing a tracking method according to an embodiment of the present disclosure.

FIG. 2 is a flowchart for describing the tracking method according to an embodiment of the present disclosure.

Referring to FIG. 2, according to the tracking method of the present embodiment, first, the camera unit 200 photographs the marker 100 fixed to the measurement object 10 and outputs the marker image (S100).

Thereafter, the tracking processing unit 500 primarily extracts the position and posture of the measurement object 10 from the marker image provided from the camera unit 200 (S200). For example, the tracking processing unit 500 may analyze the positions, sizes, etc. of position points of the marker from the marker image, and calculate the position and posture of the measurement object 10. In this case, the position and posture of the measurement object 10 may be expressed according to the camera coordinate system.

Meanwhile, the first inertia measurement unit 300, which is fixed to the camera unit 200, measures and outputs the first inertia including the first acceleration and the first angular velocity (S300).

Further, the second inertia measurement unit 400, which is fixed to one of the measurement object 10 and the marker 100, measures and outputs the second inertia including the second acceleration and the second angular velocity (S400). Here, S400 may be separately performed regardless of the order relative to S300. That is, S400 may be separately performed either simultaneously with, before, or after S300.

Thereafter, the tracking processing unit 500 secondarily extracts the position and posture of the measurement object 10, using the first inertia provided from the first inertia measurement unit 300 and the second inertia provided from the second inertia measurement unit 400 (S500).

In the present embodiment, S100 and S200, and S300, S400, and S500 may be separately performed regardless of the order thereof. Alternatively, S300, S400, and S500 may be selectively performed only when the position and posture of the measurement object 10 cannot be extracted through S100 and S200.

Further, all of S100, S200, S300, S400, and S500 may be successively performed in real time, and may also be performed intermittently, rarely, or periodically at a predetermined interval of time.

Figure 3:
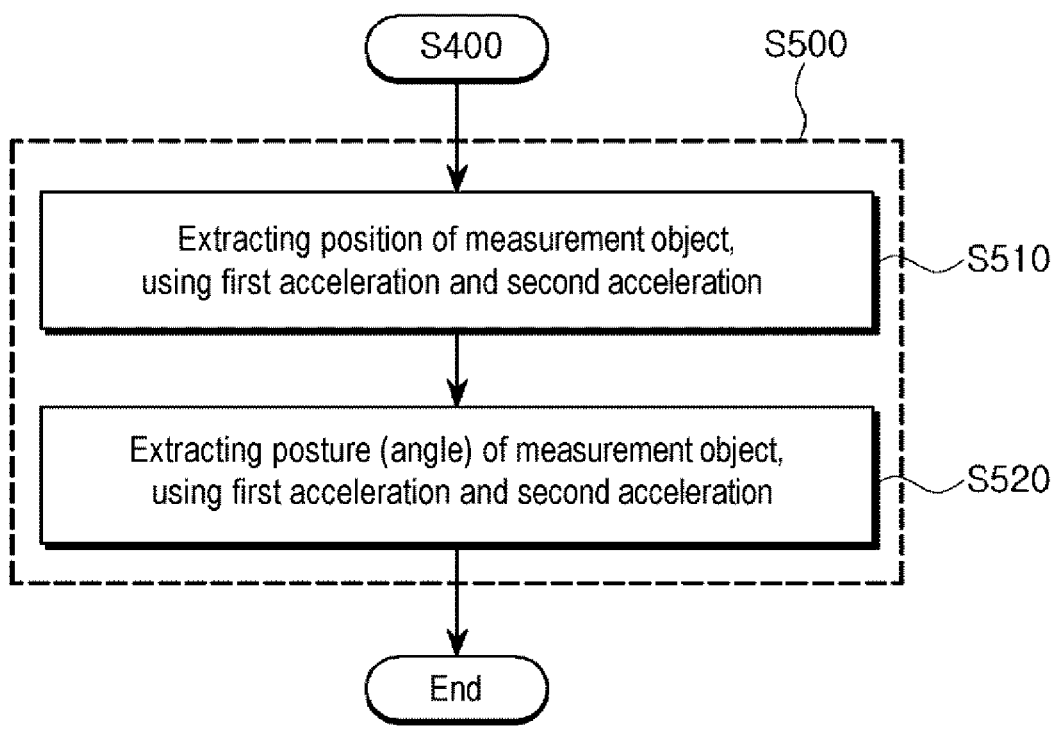
FIG. 3 is a flowchart showing a process of secondarily extracting a position and posture of a measurement object in the tracking method of FIG. 2.

FIG. 3 is a flowchart showing a process of secondarily extracting the position and posture of the measurement object in the tracking method of FIG. 2.

Referring to FIG. 3, secondarily extracting the position and posture of the measurement object 10 (S500) may include: extracting the position of the measurement object 10, using the first acceleration and the second acceleration (S510); and extracting the posture of the measurement object 10, using the first angular velocity and the second angular velocity (S520). In this case, S510 and S520 may be separately performed regardless of the order thereof.

Figure 4:
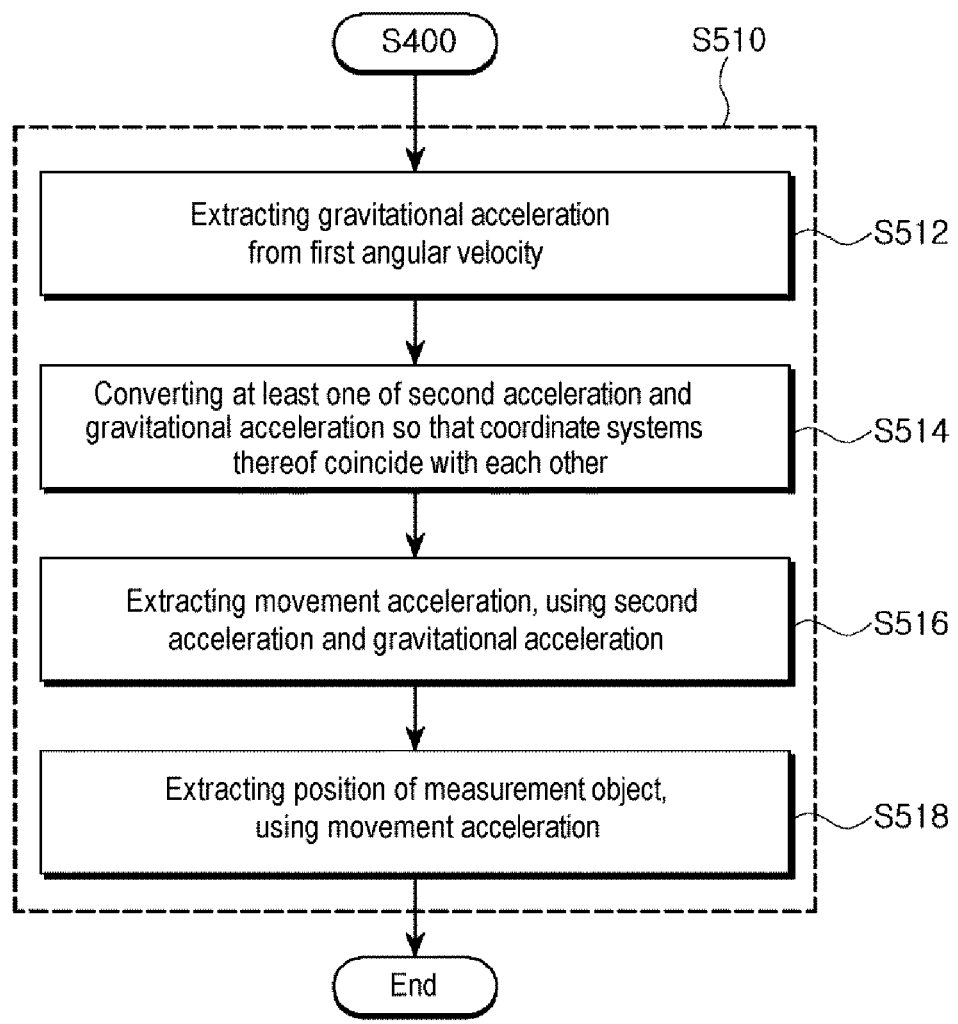
FIG. 4 is a flowchart for describing extracting of the position of the measurement object in the process of extracting the position and posture of the measurement object illustrated in FIG. 3.
Figure 5:
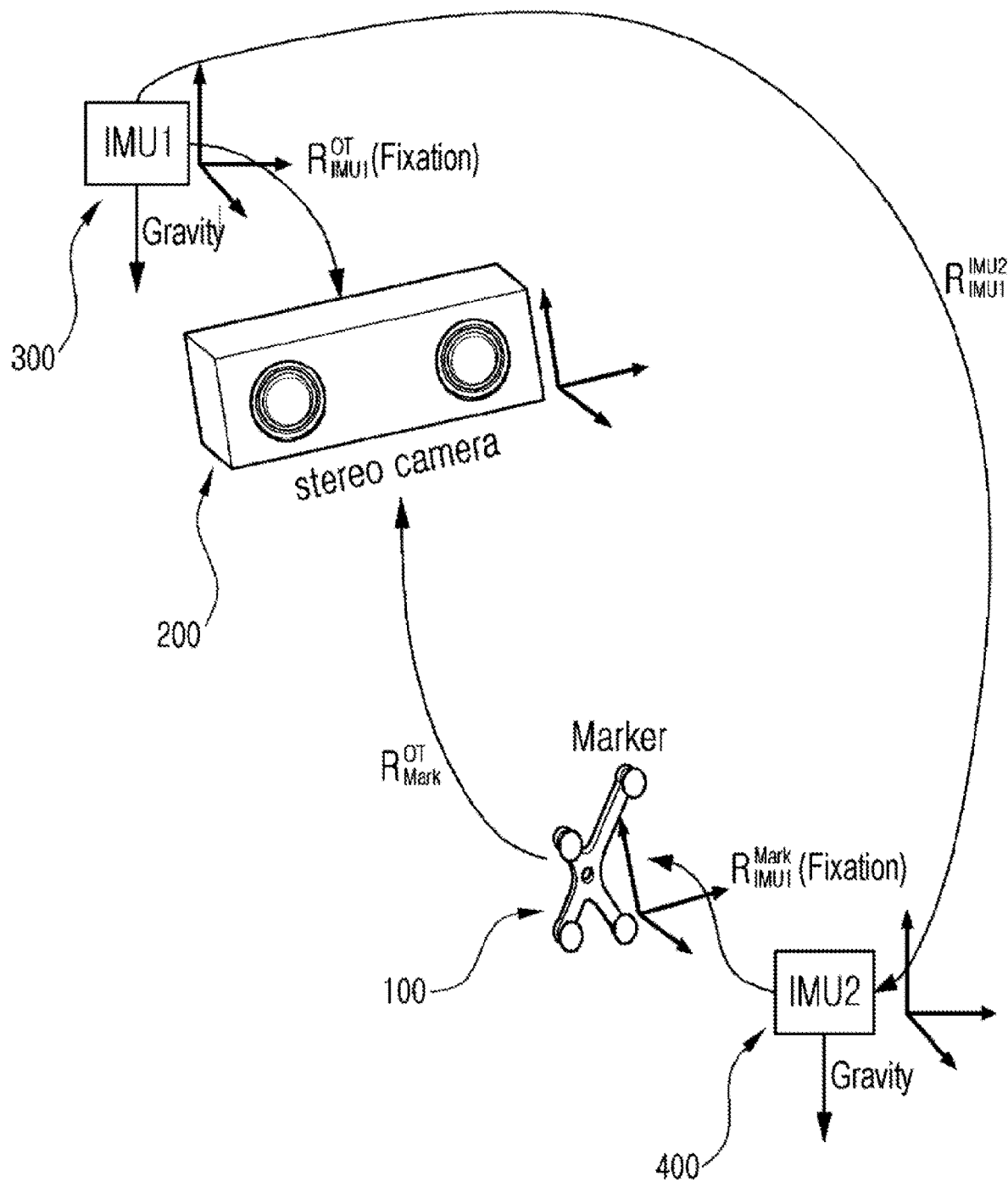
FIG. 5 is a diagram showing a concept for describing a relationship between coordinate systems and a conversion process thereof in the tracking method of FIG. 2.

FIG. 4 is a flowchart showing a process of extracting the position of the measurement object in the process of extracting the position and posture of the measurement object in FIG. 3. FIG. 5 is a diagram showing a concept for describing a relationship between coordinate systems and a conversion process thereof in the tracking method of FIG. 2.

Referring to FIGS. 4 and 5, in a step (S510) of extracting the position of the measurement object 10, firstly, the gravitational acceleration is extracted from the first acceleration (S512). In this case, the first acceleration includes the gravitational acceleration and acceleration by the movement of the first inertia measurement unit 300. When the camera unit 200, to which the first inertia measurement unit 300 is fixed, is in a stopped state, the first acceleration has a value which substantially coincides with that of the gravitational acceleration.

Secondly, at least one of the second acceleration and the gravitational acceleration is converted so that coordinate systems thereof coincide with each other (S514). In this case, the second acceleration is expressed according to the second inertial coordinate system, and the gravitational acceleration is expressed by the first inertial coordinate system. Therefore, in S514, the second acceleration may be converted from the second inertial coordinate system to the first inertial coordinate system so that a coordinate system of the second acceleration coincides with a coordinate system of the gravitational acceleration, the gravitational acceleration may be converted from the first inertial coordinate system to the second inertial coordinate system so that a coordinate system of the gravitational acceleration coincides with a coordinate system of the second acceleration, or both the second acceleration and the gravitational acceleration may be converted into a predetermined coordinate system, for example, the camera coordinate system so that coordinate systems of the second acceleration and the gravitational acceleration coincide with each other.

Meanwhile, in the present embodiment, in order to minimize an error in the process of the conversion in S514, it is desirable to convert the gravitational acceleration from the first inertial coordinate system to the second inertial coordinate system and thereby make a coordinate system of the gravitational acceleration coincide with a coordinate system of the second acceleration. This is because the second acceleration has a value which changes according to time, but the gravitational acceleration extracted from the first acceleration has an almost constant value.

Thirdly, the movement acceleration by the movement of the measurement object 10 is extracted using the second acceleration and the gravitational acceleration having the coincided coordinate systems (S516). Specifically, the tracking processing unit 500 may remove the gravitational acceleration from the second acceleration and thereby calculate the movement acceleration.

Fourthly, the position of the measurement object 10 is extracted using the movement acceleration (S518). In this case, the movement acceleration may be expressed according to coordinate systems which have been made to coincide with each other through a coordinate conversion of at least one of the second acceleration and the gravitational acceleration (hereinafter, referred to as "coinciding coordinate system"), and the position of the measurement object 10 may be expressed according to the camera coordinate system.

When the coincided coordinate system does not coincide with the camera coordinate system, extracting the position of the measurement object 10 (S518) may include: converting the movement acceleration from the coinciding coordinate system to the camera coordinate system; and extracting the position of the measurement object 10, using the movement acceleration converted into the camera coordinate system. For example, when the coincided coordinate system is the second inertial coordinate system, the tracking processing unit 500 may, first, convert the movement acceleration into the marker coordinate system. Thereafter, the tracking processing unit 500 may convert the movement acceleration, which has been converted into the marker coordinate system, into the camera coordinate system again, and then doubly integrate the movement acceleration to thereby calculate the position of the measurement object 10.

On the other hand, when the coincided coordinate system coincides with the camera coordinate system, in the step (S518) of extracting the position of the measurement object 10, the tracking processing unit 500 may doubly integrate the movement acceleration, as it is, without performing the coordinate system conversion of the movement acceleration, thereby calculating the position of the measurement object 10.

Meanwhile, if the camera unit 200 is in a stopped state, the first inertia measurement unit 300 is also in a stopped state, and thus the first angular velocity has a value of zero (0). Therefore, in S520 illustrated in FIG. 3, the posture of the measurement object 10 may be extracted using only the second angular velocity. For example, the tracking processing unit 500 may integrate the second angular velocity, thereby calculating the tilted angle of the measurement object 10.

Figure 6:
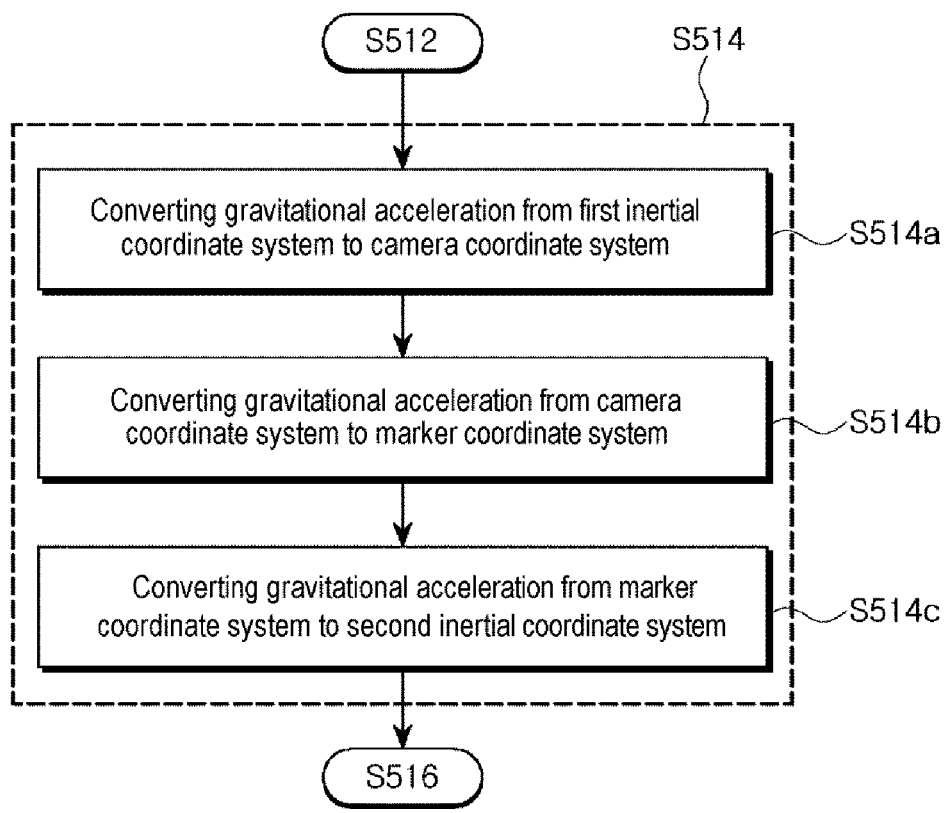
FIG. 6 is a flowchart showing a process of converting the coordinate system in the process of extracting the position of the measurement object illustrated in FIG. 4.

FIG. 6 is a flowchart showing a process of converting a coordinate system in the process of extracting the position of the measurement object illustrated in FIG. 4.

Referring to FIGS. 5 and 6, the process of converting the gravitational acceleration according to the first inertial coordinate system into the second inertial coordinate system may include: a first conversion process of converting the gravitational acceleration according to the first inertial coordinate system into the camera coordinate system; a second conversion process of converting the gravitational acceleration, which has been converted into the camera coordinate system, into the marker coordinate system; and a third conversion process of converting the gravitational acceleration, which has been converted into the marker coordinate system, into the second inertial coordinate system.

In the present embodiment, since the first inertia measurement unit 300 is fixed to the camera unit 200 and the second inertia measurement unit 400 is fixed to the marker 100 or the measurement object, each of a conversion determinant according to the first conversion process and a conversion determinant according to the third conversion process may have a constant value. Therefore, the tracking processing unit 500 may perform a coordinate conversion by using a given initial value, as it is, without performing a calculation for obtaining the conversion determinants according to the first and third conversion processes.

However, if the measurement object 10 moves when it is photographed by the camera unit 100, the marker coordinate system is also changed and thus the conversion determinant according the second conversion process may also be changed. Therefore, the tracking processing unit 500 should calculate, first, the conversion determinant according to the second conversion process before converting the gravitational acceleration into the second inertial coordinate system.

As described above, according to the present embodiment, the first inertia measurement unit 300 may be fixed to the camera unit 200, which is in a stopped state, and to measure the gravitational acceleration. Further, the second inertia measurement unit 400 may be fixed to the marker 100 or the measurement object 10 and to measure the acceleration and the angular velocity of the measurement object 10. Thereafter, the gravitational acceleration may be removed from the acceleration of the measurement object 10 so as to extract the movement acceleration of the measurement object 10, and the position and posture of the measurement object 10 may be tracked using the movement acceleration and the angular velocity of the measurement object.

Further, as the first inertia measurement unit 300 is fixed to the camera unit 200, even when the camera unit 200 moves during photographing, a conversion relationship between the first inertial coordinate system and the camera coordinate system may be maintained to be constant. As a result, the tracking process may be simplified by omitting a coordinate system correction of the gravitational acceleration according to the movement of the camera unit 200.

Although exemplary embodiments of the present disclosure have been described as shown above, it will be understood that various modifications and variations can be made by those skilled in the art to which the present disclosure pertains without departing from the spirit and scope of the embodiments described in the claims below.

(EXPLANATION OF REFERENCE NUMERALS) 100: Marker, 200: Camera unit, 300: First inertia measurement unit, 400: Second inertia measurement unit, 500: Tracking processing unit, 10: Measurement object, 20: Holding means

What is claimed is:

1. A tracking system, comprising:
    a marker fixed to a measurement object;
    a stereoscopic camera configured to photograph the marker and output a marker image;
    a first inertia sensor fixed to the camera and configured to measure and output first acceleration and first angular velocity;
    a second inertia sensor fixed to one of the measurement object and the marker, and configured to measure and output second acceleration and second angular velocity; and
    a processor configured to:
        calculate a position and a posture of the measurement object in a camera coordinate system, using the marker image;
        calculate movement acceleration by a movement of the measurement object from the second acceleration, using gravitational acceleration calculated from the first acceleration;
        convert the movement acceleration into the camera coordinate system;

calculate the position of the measurement object using the movement acceleration converted into the camera coordinate system and an initial position of the measurement object; and calculate the posture of the measurement object in the camera coordinate system using the first angular velocity, the second angular velocity and an initial tilted angle of the measurement object.

2. The tracking system of claim 1, wherein to calculate the movement acceleration, the processor is configured to calculate the gravitational acceleration from the first acceleration; and to convert at least one of the second acceleration and the gravitational acceleration so that coordinate systems of the second acceleration and the gravitational acceleration coincide with each other; and to calculate the movement acceleration, using the second acceleration and the gravitational acceleration having the coincided coordinate systems.

3. The tracking system of claim 2, wherein the first inertia sensor has a first inertial coordinate system, the second inertia sensor has a second inertial coordinate system, and wherein, to convert the at least one of the second acceleration and the gravitational acceleration so that the coordinate systems of the second acceleration and the gravitational acceleration coincide with each other, the processor is configured to convert the gravitational acceleration according to the first inertial coordinate system into the second inertial coordinate system; and to remove the gravitational acceleration, which has been converted into the second inertial coordinate system, from the second acceleration to thereby extract the movement acceleration.

4. The tracking system of claim 3, wherein the marker has a marker coordinate system, the camera has the camera coordinate system, and wherein, to convert the gravitational acceleration according to the first inertial coordinate system into the second inertial coordinate system, the processor is configured to convert the gravitational acceleration according to the first inertial coordinate system into the camera coordinate system; to convert the gravitational acceleration, which has been converted into the camera coordinate system, into the marker coordinate system; and to convert the gravitational acceleration, which has been converted into the marker coordinate system, into the second inertial coordinate system.

5. The tracking system of claim 1, wherein the first acceleration coincides with the gravitational acceleration, and the first angular velocity is zero (0).

* * * * *